US00PP33972P2

(12) United States Plant Patent
Rullo

(10) Patent No.: US PP33,972 P2
(45) Date of Patent: Mar. 1, 2022

(54) PLUM TREE NAMED 'AJOP20'

(50) Latin Name: *Prunus salicina*
Varietal Denomination: AJOP20

(71) Applicant: Fivefifty5 Super Foods Pty Ltd, Shepparton East (AU)

(72) Inventor: Joseph Rullo, Shepparton East (AU)

(73) Assignee: Fivefifty5 Superfoods Pty Ltd, Shepparton East (AU)

( * ) Notice: Subject to any disclaimer, the term of this patent is extended or adjusted under 35 U.S.C. 154(b) by 0 days.

(21) Appl. No.: 17/300,385

(22) Filed: Jun. 9, 2021

(51) Int. Cl.
*A01H 5/08* (2018.01)
*A01H 6/74* (2018.01)

(52) U.S. Cl.
USPC ..... Plt./184

(58) Field of Classification Search
USPC ..... Plt./184, 180
See application file for complete search history.

(56) References Cited

FOREIGN PATENT DOCUMENTS

AU 2019010-V * 2/2019

* cited by examiner

*Primary Examiner* — Susan McCormick Ewoldt
(74) *Attorney, Agent, or Firm* — Michelle Bos Legal LLC

(57) ABSTRACT

A Japanese plum tree named 'AJOP20' distinguished by its early season harvest maturity and its large high-quality fruit with yellow and pink-red skin color, good flavor and heavy cropping.

5 Drawing Sheets

Latin name: *Prunus salicina.*
Variety denomination: 'AJOP20'.

BACKGROUND AND SUMMARY OF THE VARIETY

The new Japanese plum tree named 'AJOP20' originated as a seedling from a 'Teak Gold' plum tree (U.S. Plant Pat. No. 10,277). The breeder extracted seeds from fruit harvested from 'Teak Gold' trees growing in a cultivated orchard near Shepparton East, Victoria, Australia in November 2012. The seeds were stratified in the bottom of the refrigerator in moist perlite for three months, and then planted in the nursery in 2013. Once the seedlings began to grow in the spring of 2013, they were transplanted to the orchard for observation. The first fruits were seen on the seedling trees in November and December 2016. One seedling in particular fruited much earlier than the other seedlings, and was labelled as 'AJOP20'. Beginning in November 2016, additional 'AJOP20' plum trees were topworked in the orchard at Shepparton East for further evaluation in subsequent years. The 'AJOP20' plum trees were particularly distinguished by their early season harvest maturity as compared to 'Teak Gold', high quality large to very large fruit with yellow and pink-red skin color, good flavor and heavy cropping, as shown in Table 1. Comparisons of 'AJOP20' to plum varieties 'Earliqueen' (U.S. Plant Pat. No. 8,583) and 'Suplumtwentytwo' (U.S. Plant Pat. No. 13,171) are shown in Tables 2 and 3.

TABLE 1

Comparison of 'AJOP20' to parent variety 'Teak Gold'

| Characteristic | 'AJOP20' | 'Teak Gold' |
|---|---|---|
| Time of harvest maturity | Very early | Mid-season |
| Fruit sweetness (Brix) | High | Medium to high |

TABLE 1-continued

Comparison of 'AJOP20' to parent variety 'Teak Gold'

| Characteristic | 'AJOP20' | 'Teak Gold' |
|---|---|---|
| Fruit skin color | Pink-red, block pattern | Mottled red, blotchy pattern |
| Fruit size | Large | Large |

TABLE 2

Comparison of 'AJOP20' to parent variety 'Earliqueen'

| Characteristic | 'AJOP20' | 'Earliqueen' |
|---|---|---|
| Time of harvest maturity | Very early | Very early |
| Fruit sweetness (Brix) | High | Low to medium |
| Fruit skin color | Pink-red, block pattern | Garnet red to maroonish blue black |
| Fruit flesh color | Medium yellow-orange | Pale yellow |

TABLE 3

Comparison of 'AJOP20' to parent variety 'Suplumtwentytwo'

| Characteristic | 'AJOP20' | 'Suplumtwentytwo' |
|---|---|---|
| Time of harvest maturity | Very early | Very early |
| Fruit flesh color | Medium yellow-orange | Red, with yellow near stone |
| Fruit size | Large | Medium |

The 'AJOP20' plum tree has been found to retain its distinctive characteristics through successive asexually propagated generations.

BRIEF DESCRIPTION OF THE PHOTOGRAPHS

The accompanying photographs were obtained in February 2021 at Shepparton East, Victoria, Australia.

Figure 1:
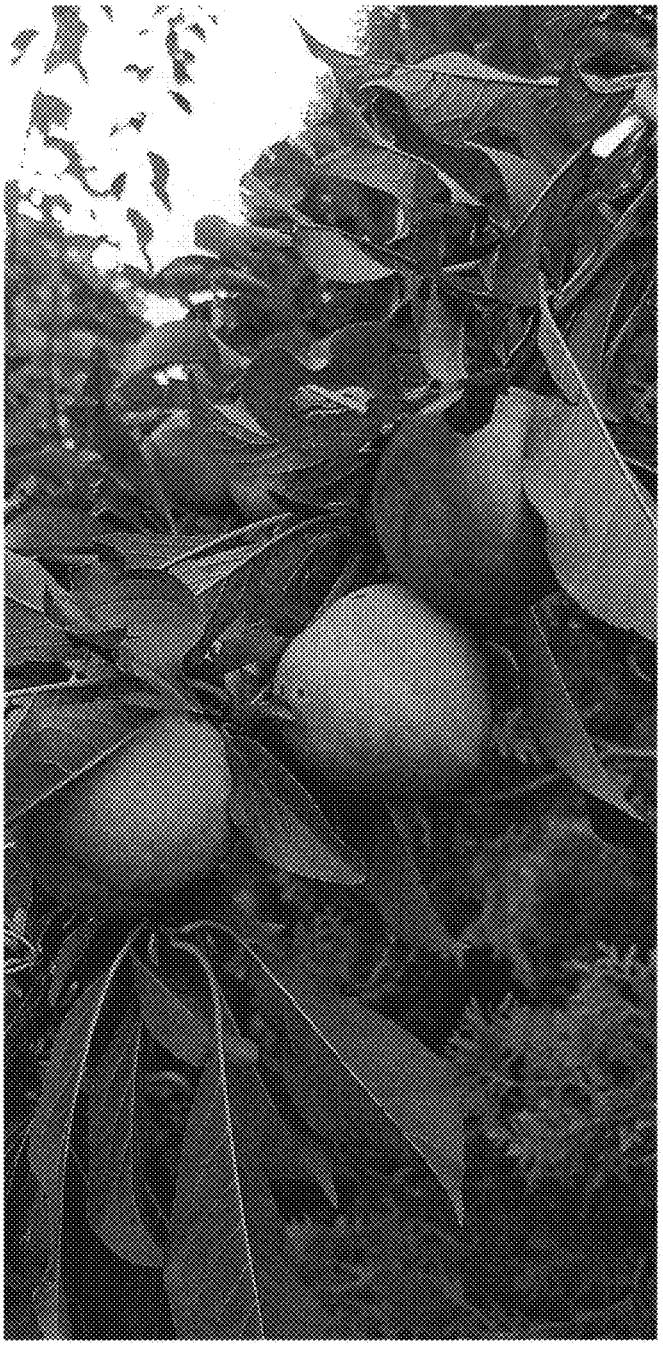
FIG. 1 shows a branch, leaves and fruit on an 'AJOP20' plum tree.
Figure 2:
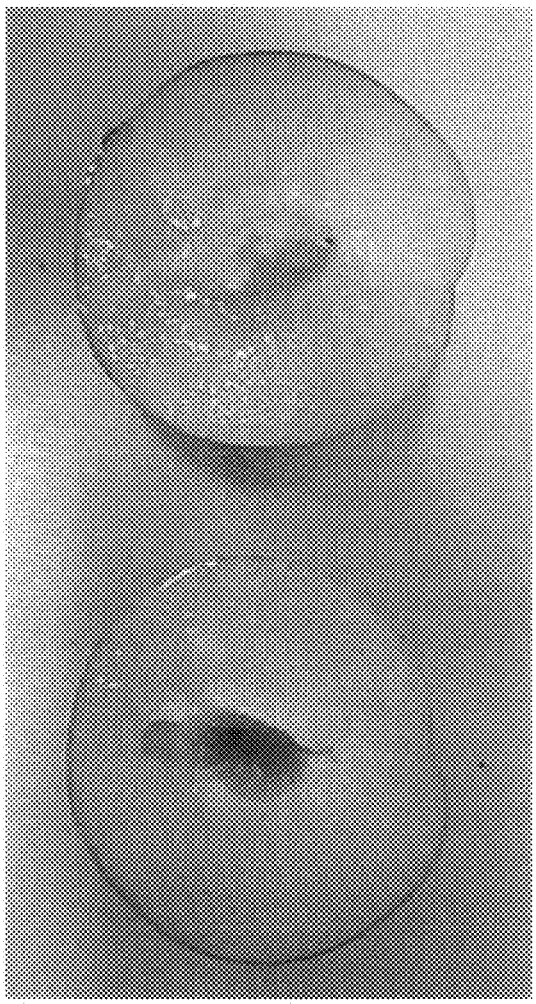
FIG. 2 shows a sectioned fruit from an 'AJOP20' plum tree.
Figure 3:
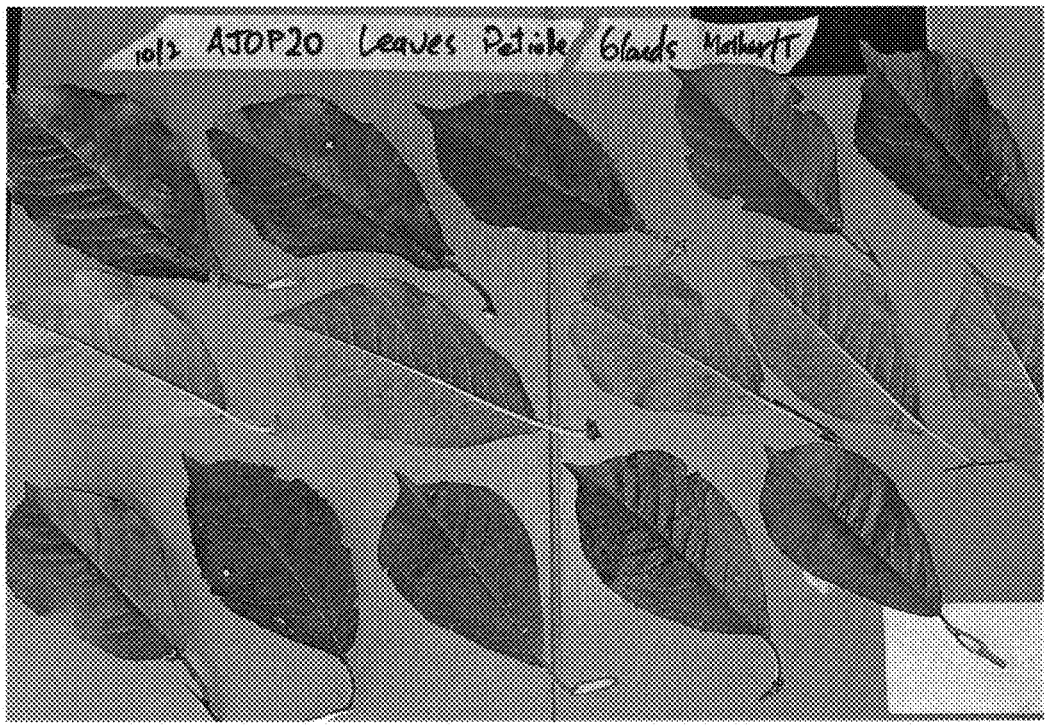
FIG. 3 shows leaves from an 'AJOP20' plum tree.
Figure 4:
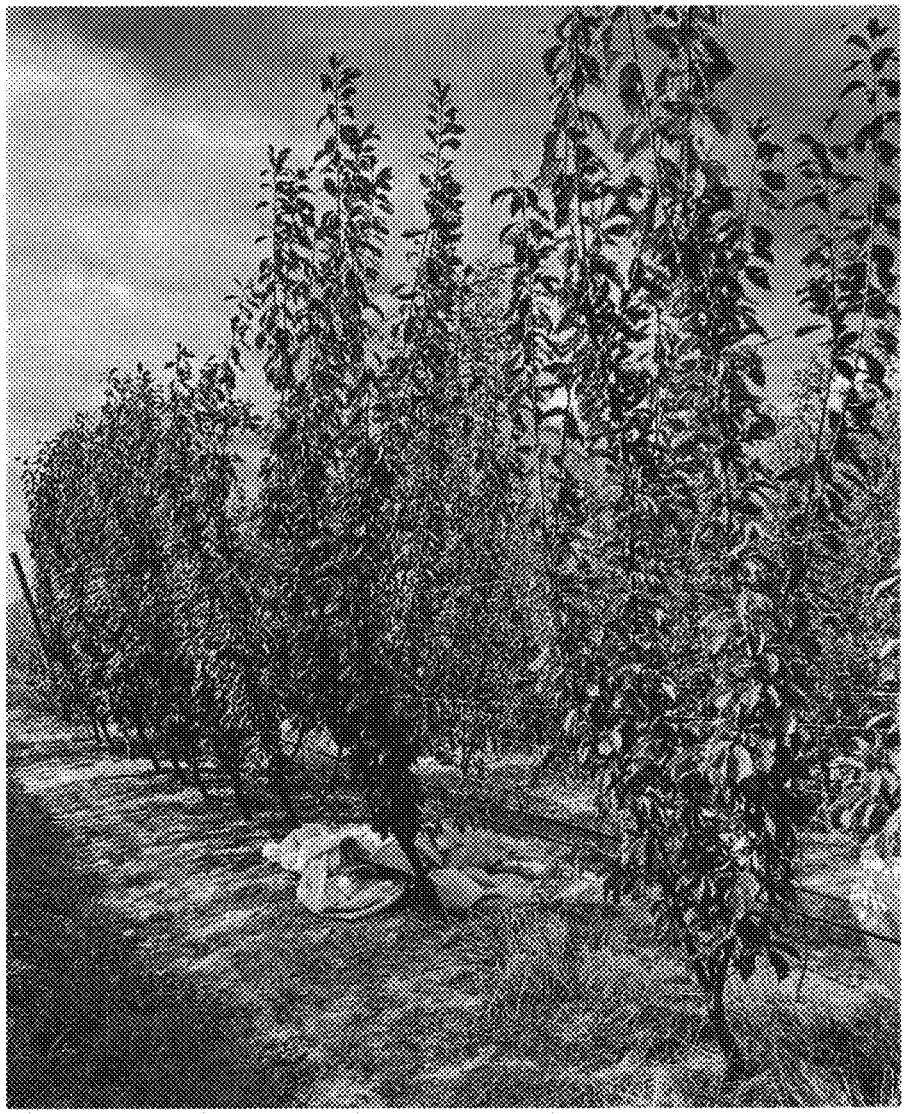
FIG. 4 shows 'AJOP20' plum trees.
Figure 5:
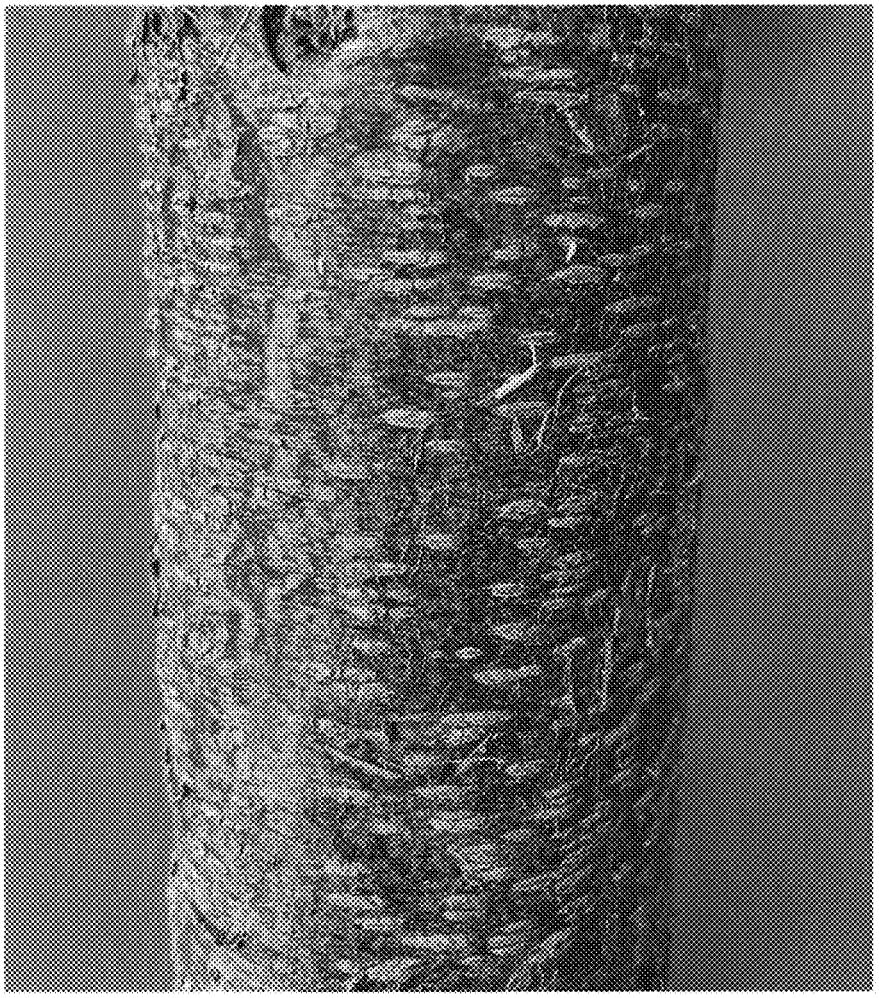
FIG. 5 shows the trunk of an 'AJOP20' plum tree.

The colors shown in these photographs may vary with lighting conditions. Color characteristics of the claimed variety should therefore be determined with reference to the observations described herein, rather than from the photographs alone.

DETAILED BOTANICAL DESCRIPTION

The following detailed botanical description is based on observations of second-generation 'AJOP20' trees, grafted onto 'H29C' Myrobalan plum rootstock (not patented) in 2016 and grown on a trellis structure. Observations were recorded during the 2020-2021 growing season near Shepparton East, Victoria, Australia. The characteristics described will vary somewhat depending upon cultural practices and climatic conditions, and will vary with location and season. Quantified measurements are expressed as an average of measurements taken from a number of individual plants of the new variety. The measurements of any individual plant, or any group of plants, of the new variety may vary from the stated average.

Color descriptions are made with reference to The R.H.S. Colour Chart (Royal Horticultural Society, $5^{th}$ ed.).

Tree:

*Size.*—Height approximately 4.0 m to top of flushing branches; spread approximately 1.1 m at top of fruit load position.

*Vigor.*—Moderate vigor.

*Habit, shape.*—Semi-spreading, rounded.

*Density.*—Moderately dense.

*Productivity.*—Moderate to heavy crop load, about 30 kg per tree.

*Bearing.*—Potential for biannual bearing.

*Number of picks.*—Single pick.

*Chilling requirement.*—400 to 500 hours with base temperature of 7° C.

Trunk:

*Diameter.*—6.5 cm at 30 cm above graft union.

*Lenticels.*—Dense, 6 per $cm^2$; horizontal; greyed-orange 166C.

*Texture.*—Smooth overall, with longitudinal cracking.

*Color.*—Brown 200B.

Branches:

*Terminal shoot length.*—1.3 m.

*Diameter at base of terminal shoot.*—10.5 mm.

*Diameter at end of terminal shoot.*—3.9 mm.

*Texture.*—Smooth on first year wood, with increasing longitudinal peeling of cuticle; cracking exposes corky underlay as tree ages.

*Lenticels on 2 year old wood.*—6 to 10 per $cm^2$, arranged horizontally.

*Attitude of one year old shoot.*—Semi-erect to erect.

*One year old shoot color.*—Greyed-orange 165B.

*One year old shoot lenticel color.*—Greyed-orange 167C.

*Color of new wood.*—Grey-brown 199A.

*Branch crotch angle.*—30° to 40° at 1 m above graft union.

*Fruiting branch color.*—Brown 200C.

*Fruiting branch lenticel color.*—Greyed-orange 166C.

Leaves:

*Arrangement.*—Alternate.

*Attitude in relation to shoot.*—Horizontal.

*Length.*—11.0 cm.

*Width.*—6.0 cm.

*Form.*—Obovate.

*Apex.*—Acuminate.

*Base.*—Acute.

*Margin.*—Broad crenate.

*Venation.*—Upper surface reticulate; lower surface mildly reticulate.

*Texture of upper surface.*—Glabrous.

*Color.*—Upper surface — Yellow-green 146A.

*Color.*—Lower surface — Yellow-green 146C.

*Color.*—Vein upper surface — Yellow-green 146B.

*Color.*—Vein lower surface — Yellow-green 145A.

*Petiole length.*—19.7 mm.

*Petiole diameter.*—2.1 mm.

*Petiole color.*—Yellow-green 148C.

*Petiole glands.*—Up to 6 or more globose glands in alternate arrangement on upper portion of petiole.

*Stipules.*—Absent or non-conspicuous.

Fruit:

*Maturity.*—Very early, February 15 to 25 at Shepparton East.

*Size.*—Large.

*Weight.*—87 g.

*Length.*—53 mm.

*Diameter at widest point.*—53 mm.

*Form, viewed from apex.*—Round to ovate.

*Form, viewed from suture side.*—Occasionally slightly asymmetrical.

*Form, viewed from side perpendicular to suture.*—Occasionally slightly asymmetrical.

*Suture depth.*—2.3 mm.

*Stalk cavity depth.*—4.8 mm.

*Stalk Cavity diameter.*—6.0 mm.

*Base shape.*—Slightly flat on shoulders.

*Apex shape.*—Slightly pointed.

*Stem length.*—10.7 mm.

*Stem diameter.*—1.6 mm.

Fruit flesh:

*Firmness.*—Very firm, Average 2.5 kgf.

*Texture.*—Firm and dense.

*Fibers.*—Fine and not obvious.

*Flavor.*—Sweet with mild acidity.

*Juiciness.*—35% to 40% juice content.

*Brix.*—17.6%.

*Flesh to stone ratio.*—1:25.

*Aroma.*—Moderately strong.

*Flesh color.*—Yellow-orange 21B.

*Cavity at tip end of stone.*—Not noticeable.

Fruit skin:

*Thickness.*—Medium.

*Texture.*—Smooth, glabrous and shiny upon brushing.

*Bloom wax.*—Heavily present on fruit at harvest.

*Ground color.*—Yellow-orange 23A.

*Overcolor.*—Orange-red 34A.

*Taste*.—Balanced sweet with low acidity.

*Lenticel quantity*.—More than 70 per $cm^2$.

*Lenticel color*.—White to brown.

Stone:

*Type*.—Semi-freestone.

*Length*.—25 mm.

*Width*.—18 mm.

*Color*.—Greyed-orange 165D.

*Shape*.—Sub-globular in ventral view; Long elliptical in basal view; pointed pistil end.

*Sides*.—Profile view asymmetrical; Ventral view symmetrical.

*Surface texture*.—Small pits throughout, including on blade.

*Ridges*.—Blade on suture complete or partial.

*Tendency to split*.—No splitting observed.

*Pest and disease resistance and susceptibility*.—Typical of *Prunus salicina* varieties.

Use: Fresh consumption.

Shipping quality: Good for domestic market.

The invention claimed is:

1. A new and distinct plum tree named 'AJOP20' substantially as illustrated and described herein.

* * * * *